United States Patent [19]
Halpern et al.

[11] Patent Number: 5,774,501
[45] Date of Patent: Jun. 30, 1998

[54] HIGH SPEED MULTILEVEL SYMBOL TELEMETRY SYSTEM FOR CARDIAC PACEMAKERS

[76] Inventors: Peter H. Halpern, deceased, late of Longwood, Fla.; by Bertha Halpern, 118 Old Hickory Ct., Longwood, Fla. 32750; Ross E. Smith, 5366 W. Portland Dr., Littleton, Colo. 80123

[21] Appl. No.: 547,394

[22] Filed: Oct. 24, 1995

[51] Int. Cl.[6] .................................................. H04L 27/10
[52] U.S. Cl. ...................... 375/279; 340/870.26; 607/32
[58] Field of Search ................................ 607/30–32, 60; 340/870.26; 375/219, 295, 316, 302, 279

[56] References Cited

U.S. PATENT DOCUMENTS

| | | | |
|---|---|---|---|
| 4,223,679 | 9/1980 | Schulman et al. | 607/32 |
| 4,281,664 | 8/1981 | Duggan | 340/870.26 |
| 4,453,162 | 6/1984 | Money et al. | 340/870.39 |
| 4,847,617 | 7/1989 | Silvian | 340/870 |
| 4,944,299 | 7/1990 | Silvian | 128/419 |
| 4,979,506 | 12/1990 | Silvian | 607/32 |
| 5,342,408 | 8/1994 | deCoriolis et al. | 607/32 |

*Primary Examiner*—Wellington Chin
*Assistant Examiner*—Conguan Tran
*Attorney, Agent, or Firm*—Gottlieb, Rackman & Reisman

[57] ABSTRACT

A high speed telemetry system for implantable devices such as a pacemaker includes a transmitter disposed in an implantable housing and an external receiver. Typically the housing is metallic and it attenuates drastically electromagnetic signals having frequencies above a relatively low cut-off frequency. The transmitter includes circuitry for generating cosine waves of different frequencies and for selectively assembling these waves to define a set of data symbols. Preferably one of the frequency is a multiple of the other. Integer halve-periods of the waves are selected to define the symbols such that the overall data transmission rate exceeds the cutoff frequency. The external receiver synchronizes itself to the transmitter, and decodes the symbols using a constellation chart to decode the symbols into binary data.

30 Claims, 6 Drawing Sheets

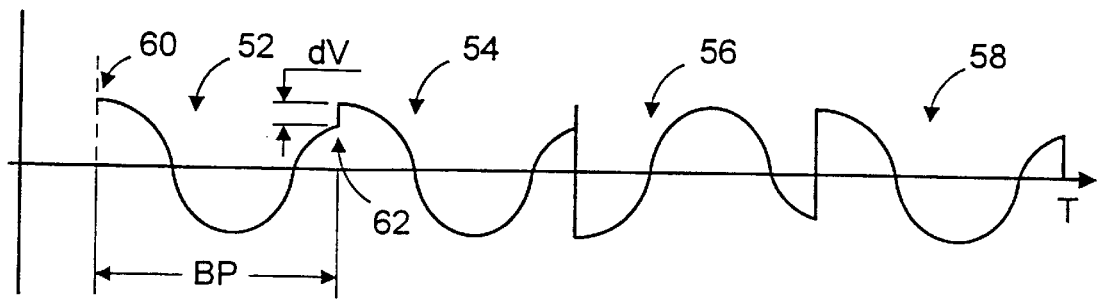
FIG. 4
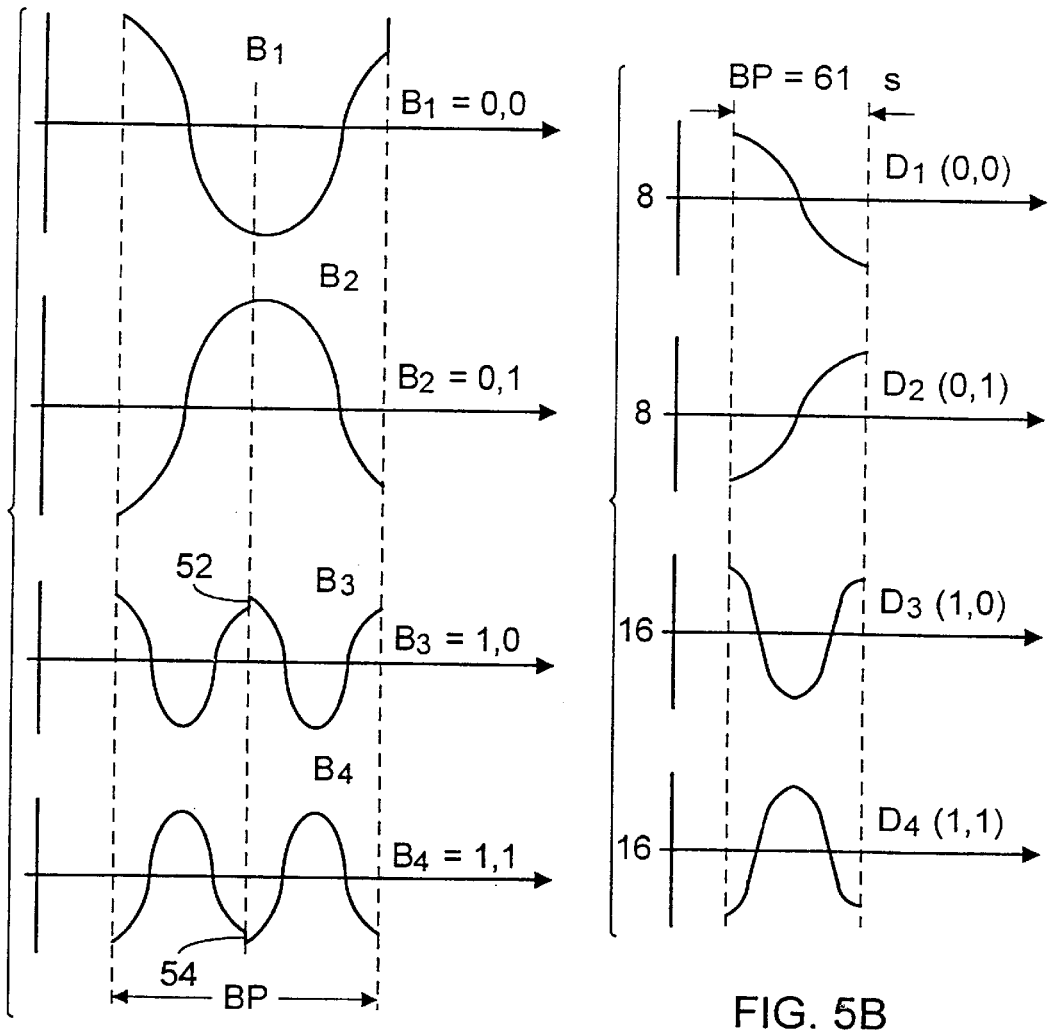
FIG. 5A
FIG. 5B

HIGH SPEED MULTILEVEL SYMBOL TELEMETRY SYSTEM FOR CARDIAC PACEMAKERS

BACKGROUND OF THE INVENTION

A. Field of Invention

This invention pertains to an apparatus incorporated in implantable pacemakers and the like constructed and arranged to provide high speed communication between the pacemakers and the outside world. The invention further pertains to a method of operating said apparatus.

B. Description of the Prior Art

Early implantable pacemakers where essentially little more than pulse generators adapted to provide pulses having a predefined amplitude, duration and pacing rate. After implantation, these pulses were applied to a patient's heart through one or more electrodes. More advanced pacemakers were developed in which the cardiac pacing pulses were not applied constantly, but only when required. In recent years, the field of pacemakers has evolved tremendously so that present day pacemakers are capable of delivering a complex sequence of pacing pulses. Moreover the functionality of the pacemakers has also increased so that some of these devices can generate not only cardiac pacing pulses, but also defibrillating or cardioverting electrical signals as well. This increase in flexibility and functionality of pacemakers also brought on an increase in the amount of information that must be exchanged between the pacemaker and the external devices, such as, for example, a programmer used by a physician to initialize a pacemaker, monitor its operation and change its operational parameters, if required.

Pacemakers are able to communicate to external devices by using an inductive coupling type of telemetry means. The devices known to the inventors are limited to schemes using pulse position, FSK or phase modulation. These schemes were limited to only one bit per baud which severely limits the transmission baud rate. Moreover the frequency of operation of these devices was limited to a low range because of the low pass filter characteristics of the pacemakers' titanium casing to about 8000 bits/second.

As mentioned above, modern day pacemakers are require to exchange a large amount of information for their operation. However because the rate of exchanging this information in present pacemakers is low, the transaction times for the information exchange is becoming excessive, leading to inconvenience to both the physician and the patient. Moreover, since a visit to a physician by the patient is becoming longer, the cost of the visit increases proportionally. This problem is becoming even more acute in pacemakers having data logging capability since the telemetry device must be used to download the logged data as well.

U.S. Pat No. 4,453,162 discloses a telemetry system utilizing a tuned LC circuit as the transceiver element.

U.S. Pat. No. 4,944,299 discloses a telemetry system using a switched LC circuit to generate PSK modulation wherein a prescribed correlation is used between the transmitter and the receiver.

U.S. Pat. No. 5,342,408 discloses a telemetry system with various types of communication protocols.

FIG. 1A shows another prior art communication scheme. This scheme consists essentially of 488 microsecond (usec) baud periods. Within each baud period, four cosine waves represent one symbol and three cosine waves represent a second symbol. Importantly, the phase and frequency of the waves remains constant.

OBJECTIVES AND SUMMARY OF THE INVENTION

In view of the above-mentioned disadvantages of the prior art, it is an objective of the present invention to provide an apparatus and method of communication which provides a much faster flow of information.

A further objective of the invention is to provide an apparatus with a low power consumption.

Yet a further objective is to provide a telemetry apparatus for a pacemaker with a minimum number of parts so that it does not increase the size of the pacemaker housing.

Other objectives and advantages of the invention shall become apparent from the following description of the invention.

Briefly, a communication system constructed in accordance with this invention consists of a pair of inductors, one in the implant and the other in the programmer. Means are provided in the implant for forming two tank circuits, each said tank circuit having a resonant frequency. In the transmitting mode, one or the other of the tank circuits are enabled to generate cosine waves. By selecting the frequency and phase of each, a plurality of symbols is defined, each symbol corresponding to one of several binary bits. In the receiving mode, a matched filter network is used to extract the cosine waves which are then decoded. Preferably, a fixed frame is transmitted by the implant, having a blanking period reserved for reverse transmission, i.e., from the programmer to the implant.

BRIEF DESCRIPTION OF THE DRAWINGS

FIG. 4 shows a proposed communication scheme;

FIG. 5A shows a time dependent chart of a first modification to the scheme modification of FIG. 4;

FIG. 5B shows a time-dependent chart of a second modification in accordance with the present invention;

DETAILED DESCRIPTION OF THE INVENTION

A. Hardware

Figure 1:
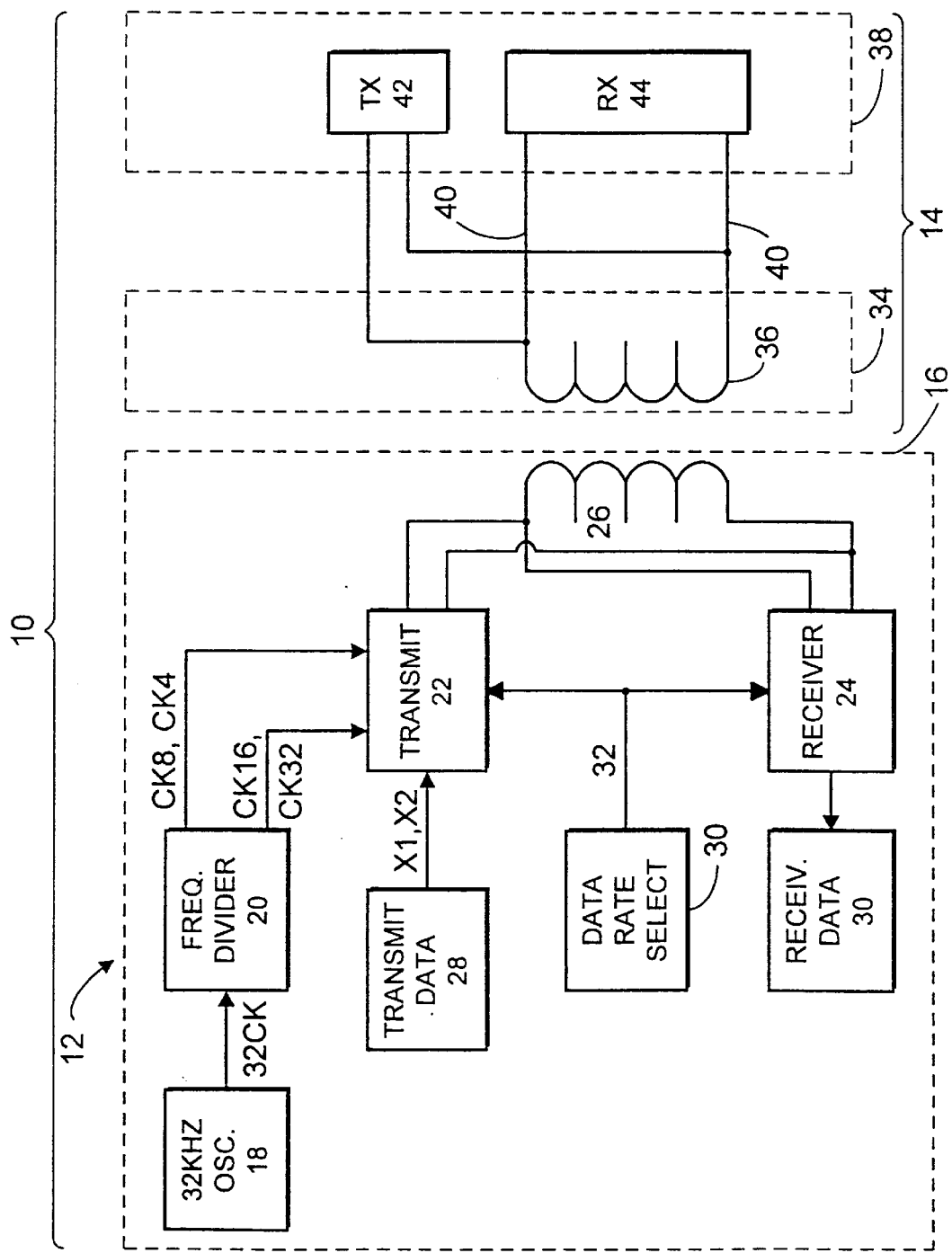
FIG. 1 shows a block diagram of the telemetering system constructed in accordance with this invention.
Figure 1A:
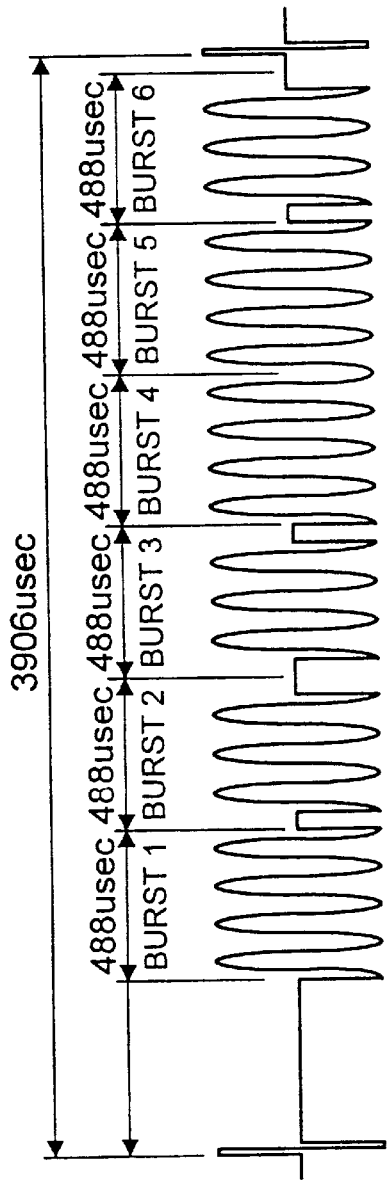
FIG. 1A shows a prior art communication scheme.

Referring now to the drawings, and more particularly to FIG. 1, a pacemaker system 10 is illustrated consisting of an implant 12 and a programmer 14. The implant 12 consists of a housing 16 which is preferably made of a titanium alloy or other similar material. Inside the housing there is provided a crystal oscillator 18 operating at a frequency of 32.798 kHz. This signal is normally referred to as a 32 kHz signal and is identified in the Figure as 32Ck. This oscillator provides clocking pulses for various pacemaker functions which do not form part of the present invention. The output of the oscillator 18 is also fed to a frequency divider network which divides this frequency to provide a nominal 8 Khz and 16 Khz clocking signal, identified in FIG. 1 as 8Ck and Ck16 respectively. The actual frequency of these signals are 8.192 kHz and 16.384 kHz, respectively.

The implant 12 further includes a transmitter 22, a receiver 24 and a common coil 26. Data for transmission by transmitter 22 is stored in a transmit data memory 28 and data received by receiver 24 is stored in a data receive memory 30.

As shall be describe in more detail below, preferably the implant 12 is designed and constructed to transmit and receive data at one of several baud rates. For this purpose, the implant 12 includes a data rate selector 30. The data rate selector generates a control signal on line 32 to designate the data rate to be used by the transmitter 22 and receiver 24.

The programmer 14 includes a programmer wand 34 holding a coil 36. The programmer 14 further includes a programmer housing 38 coupled to wand 34 by a pair of wires 40. Inside the programmer housing there is provided a transmitter section 42 and a receiver section 44, each being coupled to the coil 36 through wires 40 as shown.

Figure 2:
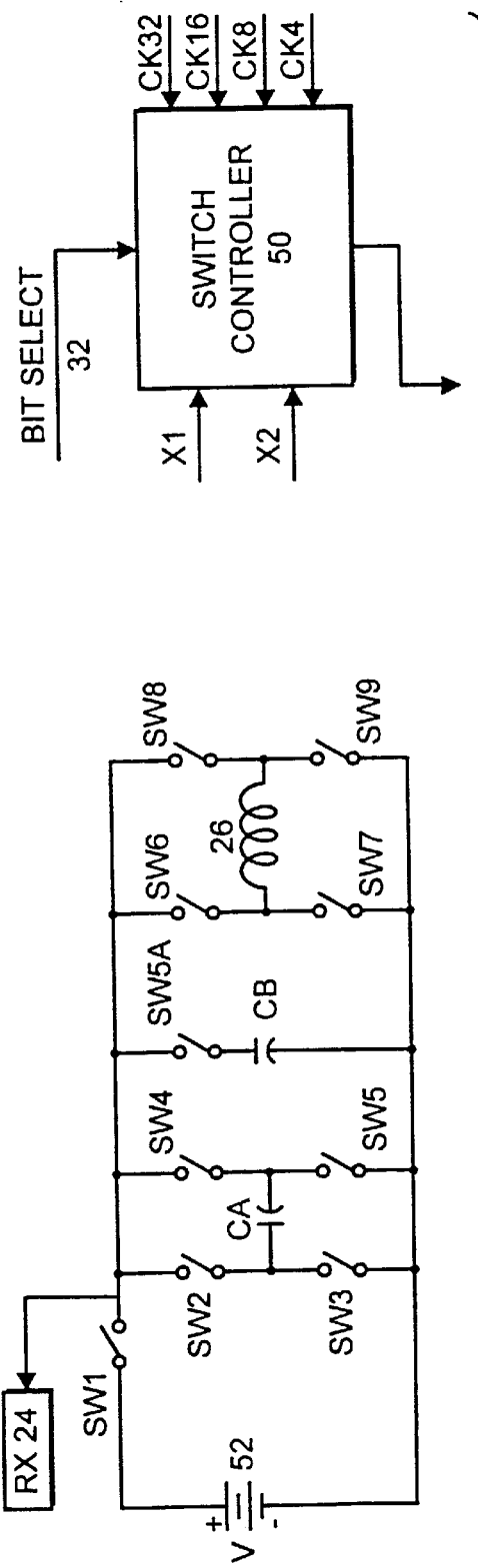
FIG. 2 shows details of the transmitter for the implant telemetering section of FIG. 1.

Referring now to FIG. 2, the transmitter section 22 includes a plurality of switches labeled SW1–9, a first capacitor CA and a second capacitor CB. Switches SW1–9 are electronic switches operated by a switch controller 50. Switch SW1 selectively connects the switching network to battery 52. Controller 50 receives the clock signals 32CK, 16CK, 8CK and 4CK, data signals X1, X2 from memory 28, and the bit rate selector signal on line 32 from data rate selector 30.

Figure 3:
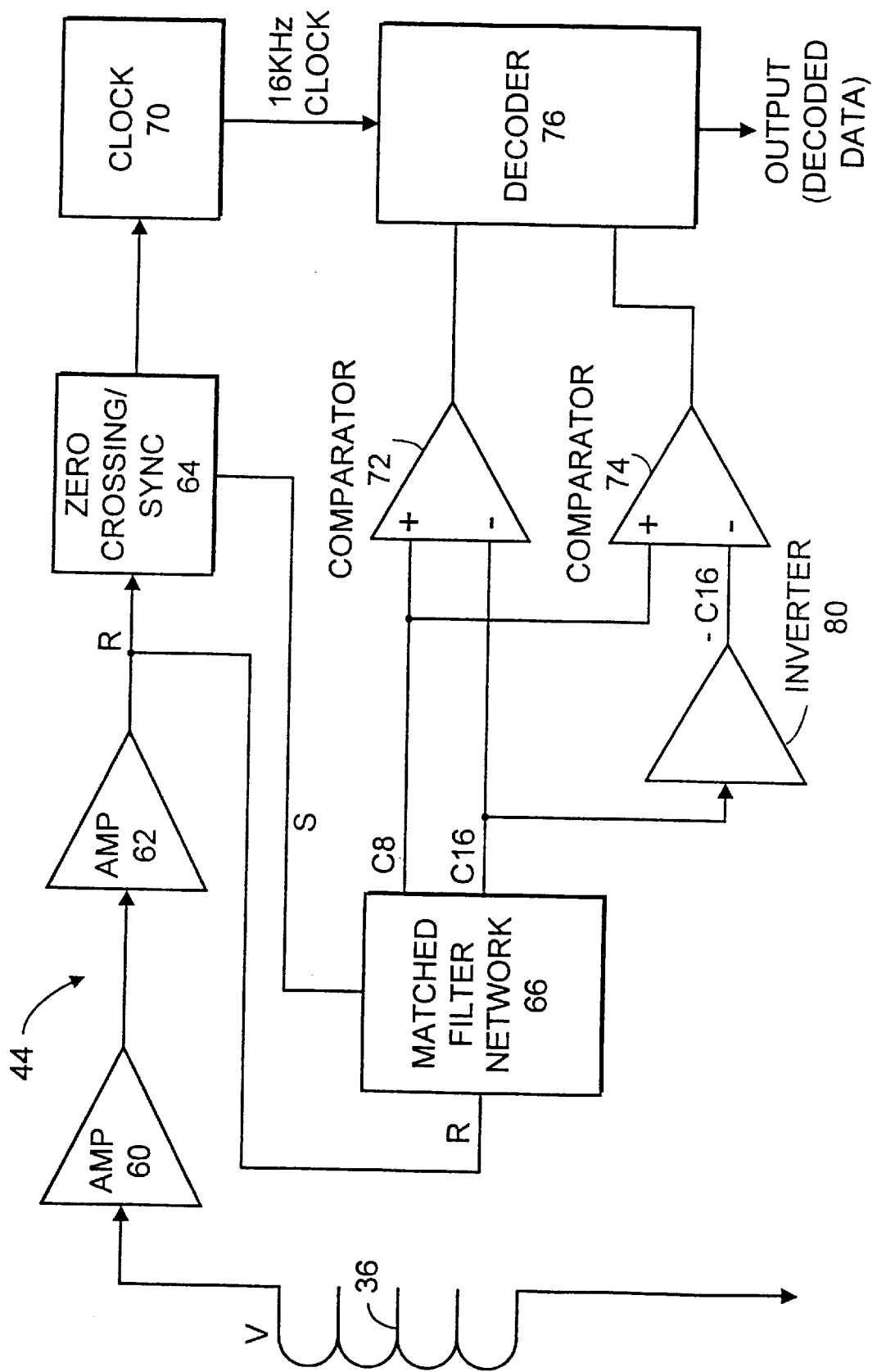
FIG. 3 shows a block diagram of the telemetering system of a programmer constructed in accordance with this invention.

Referring now to FIG. 3, the receiver section 44 in the programmer 14 includes an amplifier 60 receiving a signal V picked up by coil 36. The output of amplifier 60 is fed to a low pass filter 62 provided to eliminate higher frequency noise above 32 kHz. The filtered signal R is fed to a zero crossing sync circuit 64 and a matched filter network 66. The outputs of the filter network are fed to a pair of comparators 72, 74 and to an inverter 80. The outputs of the comparators are fed to a decoder 76.

Before the operation of the transmitter and receiver of FIGS. 1, 2 and 3 is described, first the communication scheme is explained.

B. Communication Scheme

Pacemaker systems have special communication requirements, including low power, low frequency and low bandwidth. In addition, for inductive coupling, all switching must occur while the current through the inductor is minimal.

A PSK-type communication scheme is shown in FIG. 4. In this scheme, signals are transmitted sequentially with a baud period BP of 122 us (microseconds). As seen in FIG. 4, each symbol consists of either a full positive cosine wave (such as symbols 52, 54, 58) or a negative cosine wave (symbol 56). These full waves are assigned binary values. For example, waves 52, 54, 58 maybe assigned a binary value of '1' and wave 56 may be assigned a binary value of '0'. It should be noted that the waves are not ideal but rather they drop in amplitude from the maximum point 60 to point 62 by a differential amount dV. This drop is due to the resistive losses in the tank circuit used to generate the waves, as described below. The frequency of the waves 52–58 is nominally 8 kHz. Importantly, every wave 52–58 starts at its maximum absolute amplitude, i.e. when the current through the inductor used for coupling is zero. In this manner the transmitter can switch from one symbol to the other without waiting for the current in the inductance to decay. This is an important consideration in pacemakers since the current through the implant inductor should not be switched. In addition, switching during low current levels is advantageous because it saves power and reduces intersymbol interference. A drawback of the scheme shown in FIG. 4 is that it provides a data rate which is still relatively slow as discussed above.

An improved communication is shown in FIG. 5A. In this Figure, the first symbol B1 (similar to symbols 52, 54 and 58) is a positive cosine wave and the second symbol B2 (similar to symbol 56 in FIG. 4) is a negative cosine wave, each wave consisting of a full cycle having nominal frequency of 8 kHz. FIG. 5A shows two more symbols, B3 and B4, which are used in accordance with this invention in conjunction with symbols B1 and B2 to effectively double the data rate of the scheme, while using the same baud rate. Symbols B3 and B4 consist of positive cosine and negative cosine waves, each cosine wave consisting of two cycles having a nominal frequency of 16 kHz and a baud period of 122 us.

Figure 6:
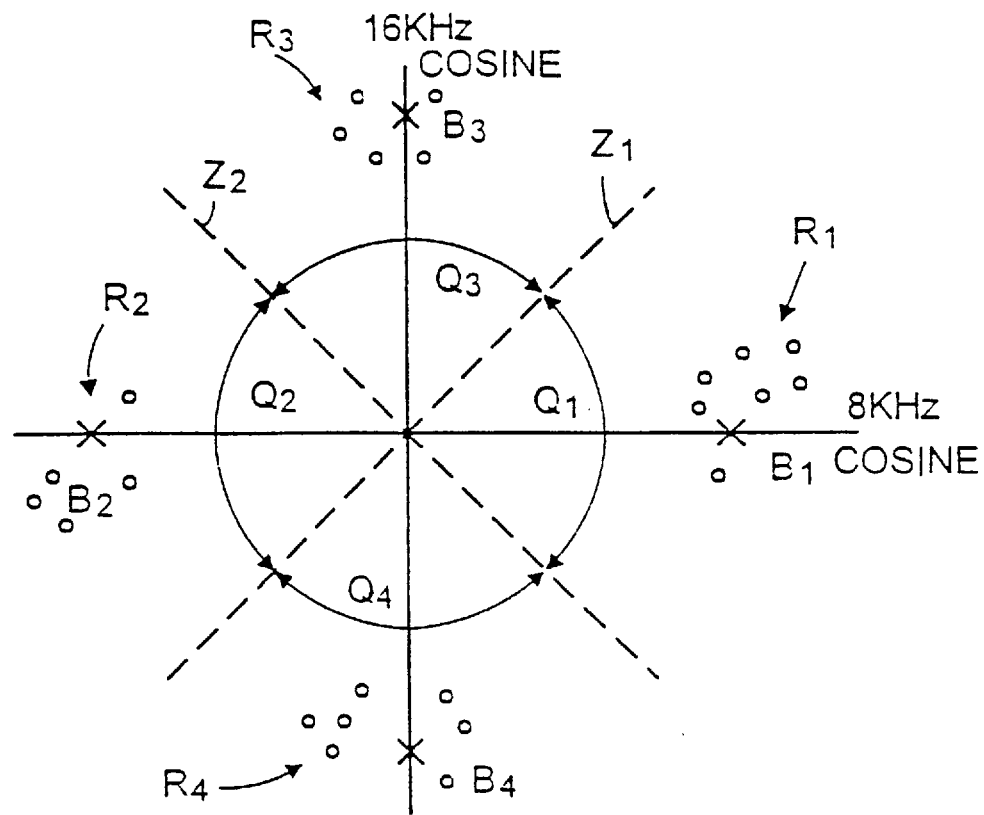
FIG. 6 shows a constellation diagram for the transmitted and received symbols for FIGS. 5A and 5B.

The symbols B1, B2, B3 and B4 may be advantageously represented on a constellation chart as shown in FIG. 6, wherein the symbols B1 and B2 defined by the 8 kHz cosine waves are disposed on the horizontal axis and the symbols B3 and B4 defined by the 16 kHz cosine waves are disposed along the vertical axis. The symbols B1, B2, B3 and B4 are assigned two bits each, such as (0,0), (0,1), (1,0) and (1,1) respectively. Hence the data rate of the scheme of FIG. 5A increased from 8000 bits/second to 16,000 bits/second at the same baud rate of 8000.

Another communication scheme is shown in FIG. 5B. In this Figure the baud period has been reduced by 50% from the one in FIG. 5A, i.e. to 61 us. However, the frequency of the signals is still limited by the titanium housing. Therefore the four symbols D1–D4 are defined as follows: D1=½0 positive 8 kHz cosine wave, D2=½ negative 8 kHz cosine wave, D3=1 positive 16 kHz cosine wave; D4=1 negative 16 kHz cosine wave. As before, two bits may be assigned to each symbol, as shown. In this manner, the nominal rate is increased to 32K bits/sec while the frequency of the symbols remain the same. The position of these symbols D1–D4 on the constellation diagram of FIG. 5B is identical to the positions of symbols B1–B4.

C. Operation - Transmitting

The operation of the transmitter circuit as shown in FIG. 2 shall now be described. The switch controller 50 receives all the clock signals CK4, CK8, CK16 and CK32, as well as the data signals X1, X2 and the data rate control signal DR on line 32. Based on the data rate designated by the control signal DR, and the binary data X1, X2, the controller then selectively operates the switches SW1–SW9 for transmitting each corresponding baud. This latter signal defines the data rate of the transmitter.

The various bit rate for the system and the corresponding baud periods BP, as well as the required symbols for each transmission scheme are summarized in the following table, with the two first rows being prior art schemes such as the one shown in FIG. 4.

| Bit Rate (BPS) | Frame Length (ms) | Baud Interval (us) | Symbols |
| --- | --- | --- | --- |
| 1.5 K | 4 | 488 | 4 cycles of± 8 kHz |
| 8K | 10 | 122 | 1 cycle of ± 8 kHz |

-continued

| Bit Rate (BPS) | Frame Length (ms) | Baud Interval (us) | Symbols |
|---|---|---|---|
| 16K | 10 | 122 | 1 cycle of ± 8 kHz |
| | | | 2 cycles of ± 16 kHz |
| 32K | 10 | 61 | ½ cycle of ± 8 kHz |
| | | | 1 cycle of ± 16 kHz |

All of these schemes are implemented by selectively closing switches SW1–SW9 to form a tank circuit having a resonant frequency of 8 kHz, or 16 kHz. For this purpose, the value of capacitor CA is selected to resonate with inductor 26 at 8 kHz, while capacitor CB is selected to resonate with inductor 26 at 16 kHz.

Instead of using two capacitors, a tapped inductor may be used to form a tank circuit having one of two resonant frequencies.

In order to illustrate how the circuit operates, the generation of symbol D1 is now explained. At the beginning of each baud period switch SW1 closes for a very short time period. At the same time switches SW2 and SW5 also closed thereby charging capacitor CA to voltage +V. After the capacitor CA is charged, switch SW1 opens and the charged capacitor is now connected to the inductor 26 by closing switches SW6 and SW9. The tank circuit thus formed starts resonating at 8 kHz and is interrupted after 61 us (microseconds) to define one half cycle of the positive cosine wave shown in FIG. 5B. When the half wave is completed the switches SW6 and SW9 are opened thereby completing symbol D1. At this point the capacitor CA is charged to a negative voltage (−V) offset by Vd from the initial voltage due to resistive losses in the tank circuit. Before the next symbol is generated, the polarity of the voltage on CA is reversed by enabling switches SW4 and SW3. This reversal causes the polarity of the voltage on CA to be the same as the polarity of the battery from which CA will be charged. In this manner, significant battery energy is saved. The circuit is now ready to generate the next symbol. As previously mentioned, capacitor CA is used to generate the 8 kHz symbols D1, D2. If the next 8 kHz symbol consists of a ½ cycle of a negative cosine wave (i.e., D2) then the capacitor CA is coupled to the coil L through switches SW3, SW4, SW7 and SW8. If the next 8 kHz symbol is D1, the capacitor CA is discharged through switches SW3, and SW4 and switches SW6 and SW9. Thus the capacitor CA is charged to the voltage +V through switches SW3 and SW4, and is discharged either through SW6/SW9 or SW7/SW8. After each baud period, the voltage across capacitor CA may be replenished by closing either SW2/SW5 or SW3/SW4.

The 16 kHz waveforms are generate by using capacitor CB. In order to charge or refresh the capacitor CB, a separate switch bridge may be provided similar to the one shown for capacitor CA. Alternatively, since capacitor CB is always used to generate at least one full cycle for each symbol, a single switch SW5A may be used to control the tank circuit, and a switch bridge may be provided for the inductor L. Thus, in order to generate symbol D3, the capacitor CB is first charged by closing switches SW1 and SW5A. Next, the resonating tank circuit is formed by opening SW1 and connecting capacitor CB to the coil 16 through switches SW6 and SW9 for a period equal to the resonant period of the tank circuit. At the end of the period, the capacitor is charged to +V less dV. If the next baud is D3, the same processes are repeated. If the next symbol is D4, then the capacitor CB is connected to the inductor 16 through switches SW7 and SW8 thereby providing a phase reversal.

The scheme shown in FIG. 5A may be implemented the same way except for the duration of the baud period. Alternately, in this scheme, at the end of each cosine wave, the capacitor CB is refreshed as discussed above, and as shown in FIG. 5A at 52, 54.

Preferably, the system 10 is operated in half-duplex mode. During receiving, the capacitors CA, CB and battery 52 are disconnected and the inductor is connected through switches SW 6 and SW 9 to the receiver 24.

D. Receiving

Referring now to FIG. 3, the inductor 36 is inductively coupled to the inductor 26 and is disposed in a programmer wand. In the receiving mode the inductor 36 is coupled to an operational amplifier 60 (the switches of FIG. 3 have been omitted for the sake of simplicity). Amplifier 60 which incorporates a low pas filter to eliminate noise. The output of amplifier 62 is fed to a zero crossing detector/synchronizer 64, as well as to a matched filter network 66 used for decoding the signals received from the inductor L.

Referring to FIG. 6, the symbols generated by the transmitter of FIG. 2 are represented as idealized points B1–B4. However, due to the narrow bandwidth of the communication channel utilized, and to intersymbol interference, the signals received by the inductor 36 appear on the diagram as four clouds of points, such clouds R1, R2, R3, R4, each being disposed in a somewhat irregular fashion around the respective transmitted points B1–B4. Two diagonal axes Z1 and Z2 drawn through the origin of the constellation diagram partition the constellation diagram into four quadrants Q1–Q4, each quadrant containing one of the clouds. Any symbol received can then be designated as corresponding to one of the points B1–B4 dependent on the respective quadrant. For example, each point of cloud R1 is disposed in quadrant Q1 and hence it corresponds to transmitted symbol B1, each point of cloud R2 can be designated as corresponding to transmitted point B2, and so on.

The signals thus generated are decoded as shown in FIG. 3. The matched filter network 66 is used to extract from its input signal R: a +8 kHz sine signal (S); a +8 kHz cosine signal (C8); and a +16 kHz cosine signal (C16). This last signal is also inverted by inverter 80 to generate −16 kHz cosine signal (−C16). Since the maximum amplitudes of these signals may be different, an equalizer means, such as a resistive network may be included in the filter network to insure that the components have the same peak magnitudes.

The signals S, C8, C16 and −C16 are derived by the filter network using standard filtering and phase matching techniques.

Figure 7:
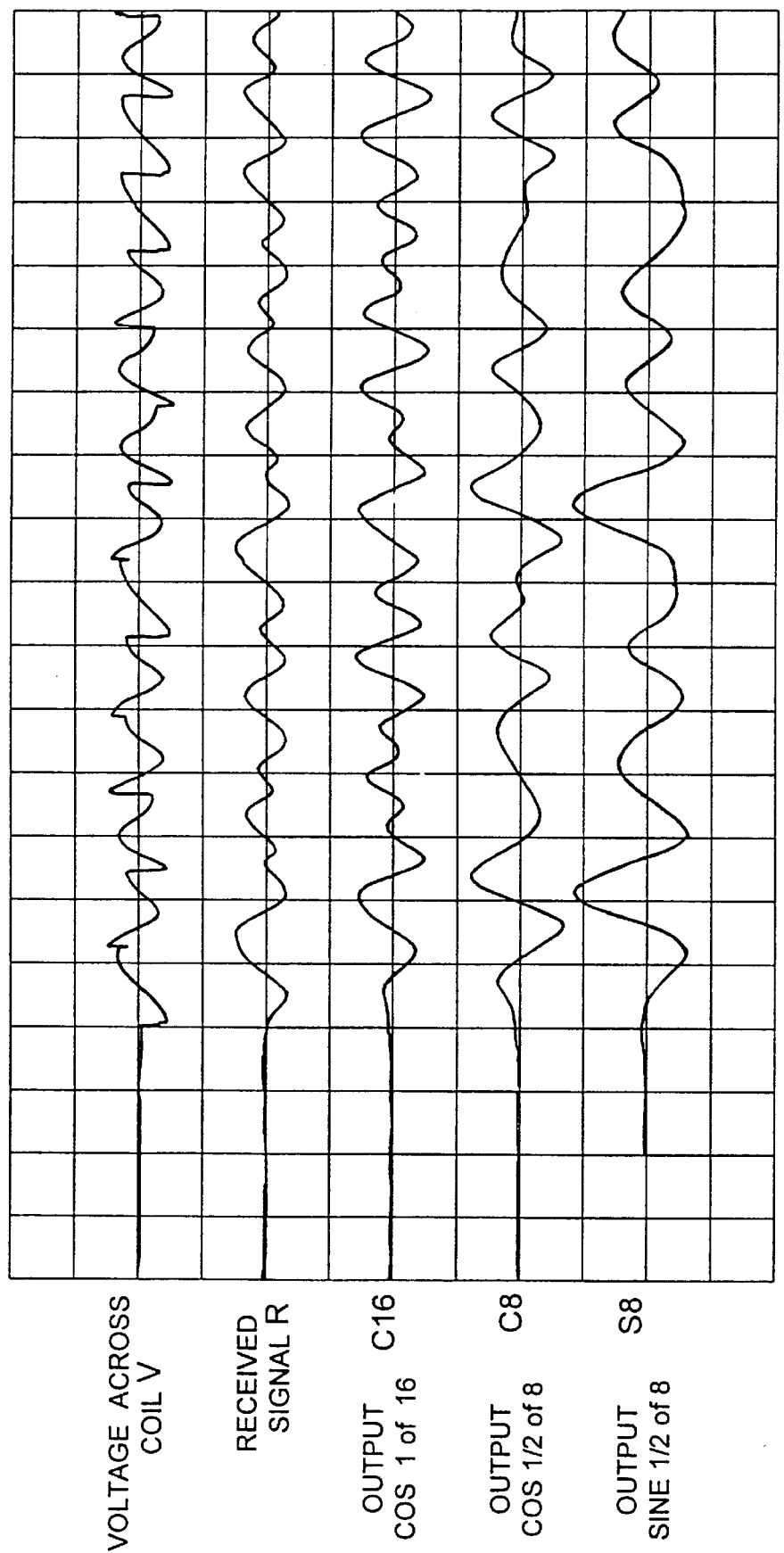
FIG. 7 shows typical received signal and the corresponding signals from the matched filter.

A typical received signal R and the resulting components are illustrated in FIG. 7, together with the signal across coil L and the output R of amplifier 62. These signals are typical for a 6 cm separation between a transmitter and receiver coil. Therefore at the beginning of each frame (described below) the component S is fed to the zero crossing/sync circuit 64 which generates a SYNC signal indicative of these zero crossings. This sync signal is used to synchronize the output CK of a 16 kHz clock generator 70. The CK clock signal enables the two comparators 72, 74. Comparator 72, when enabled (or latched) compares the components C8 and C16. In effect the comparator 72 makes a decision as to whether a receive symbol is on one side of axis Z1 or the other. More particularly, if component C8 is larger than C16 then the received symbol must be in quadrants Q1 or Q4. Otherwise, the received symbol must be in quadrant Q2 or Q3.

Similarly, comparator 74 makes a decision on whether the received symbol is on one side or the other of axis Z2. If the component C8 is larger than component C16 then the received symbol must be in quadrants Q2 or Q4. Otherwise the received symbol must be in quadrant Q1 or Q3. The outputs of comparators 72 and 74 are fed to a decoder 76 which then makes a decision identifying the quadrant corresponding to the received symbol R and generates two binary bits for the symbol. This decision is based on the following table:

|  | COMPARATOR 72 | |
|---|---|---|
| COMPARATOR 74 | 0 | 1 |
| 0 | Q1 | Q2 |
| 1 | Q3 | Q4 |

E. Synchronization and Framing

Figure 8:
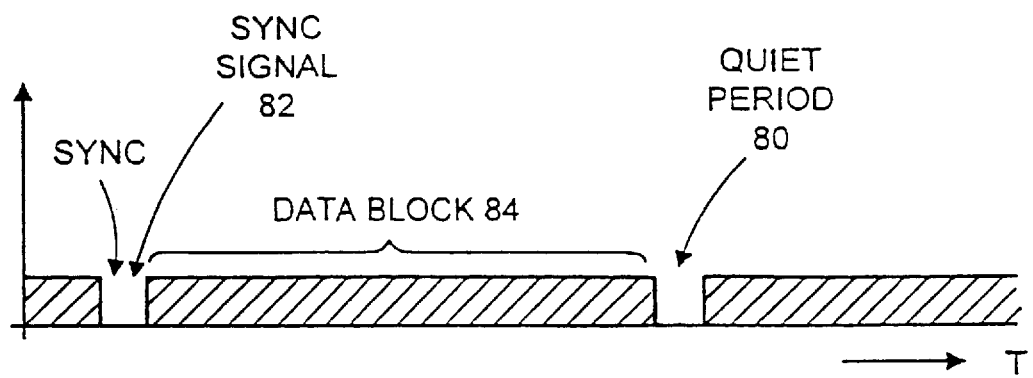
FIG. 8 shows as the structure of a communication frame in accordance with the invention.

The communication described so far is equally applicable independently of whether the symbols originate from the pacemaker or the programmer. However in order to reduce the power requirements and the complexity of the pacemaker, synchronization and framing are controlled from the pacemaker as follows. A typical frame transmitted by the pacemaker is shown in FIG. 8. It consists of a quiet period 80 having a duration, for example of 488 us. The quiet period is used to announce to the programmer that a new frame is to be expected. This quiet period 80 may also be used by the programmer to generate its own data to the pacemaker.

The quiet period is followed by a dedicated initial symbol 82. Preferably the symbol 82 is a half cycle of an 8 kHz cosine signal shown in FIG. 7. This signal is used by the network 66 to generate the sine output (signal S) needed to synchronize the programmer clock to the received signal as described above. The external sync signal is followed by a data block 84 of a predetermined number of symbols. The duration of the data block 84 is preferably in the range of 75 periods of the 8 kHz signal, i.e. , 9.75 ms. The number of symbols is dependent on the encoding scheme used, as described above.

This sync and framing technique is advantageous because it allows communication to occur at an efficiency exceeding 90% while in prior communication schemes only a 75% efficiency was achieved. Because the bandwidth is so limited intersymbol interference, occurs. Viterbi decoding may be used to significantly reduce the effect of this ISI. If the communication channel is noisy or other sources of errors degrade the performance of the scheme, an error detection/correction scheme may be used.

The data rate for the scheme may be determined by the programmer based, for example, on error rates.

Signals from the programmer to the implant may be transmitted using any prior art schemes such as pulse position modulation. This scheme is preferred because it is simple to implement and has low power requirements.

Although the invention has been described with reference to several particular embodiments, it is to be understood that these embodiments are merely illustrative of the application of the principles of the invention. Accordingly, the embodiments described in particular should be considered exemplary, not limiting, with respect to the following claims.

We claim:

1. A data communication system for an implantable device with a housing, said system comprising:
    a transmitter disposed in said housing and including a generator for generating a first symbol consisting of a first integer number of half cycles of a first sinusoidal wave and a second symbol consisting of a second integer number of half cycles of a second sinusoidal waves, said first and second waves having a different phase; and
    a receiver for receiving said signals, said receiver including a distinguishing member for distinguishing said first and second symbols, said distinguishing member including a filter generating first and second sinusoidal received signals based on said symbols and a comparator for comparing the magnitudes of said received signals.

2. The system of claim 1 wherein said symbols have the same duration.

3. The system of claim 1 wherein said first and second sinusoidal waves are cosine waves.

4. The system of claim 3 wherein said first symbol and second symbols are selected from a positive and a negative cosine wave.

5. The system of claim 1 wherein said symbols can be characterized as points on a two dimensional chart, said decoder means including means for partitioning said chart into several zones, each received point falling into one of said zones, and means for assigning received data bits to each received symbol dependent on the zone corresponding to said symbol.

6. The system of claim 5, wherein said chart is defined by two orthogonal axes, one axis corresponding to said first frequency and the second axis corresponding to said second frequency.

7. The system of claim 1 wherein said transmitter includes symbol sending means for emitting said symbols consecutively, said symbols being arranged in consecutive frames, each frame being preceded by a quiet period and a unique synchronizing symbol.

8. The system of claim 7 wherein said unique symbol is at least one half cycle of a cosine wave.

9. The system of claim 7 further comprising, synchronizing means for synchronizing said transmitter and said receiver based on said unique symbol, and decoding means for decoding said symbols into received digital data.

10. The system of claim 1 wherein said first and second waves are out of phase by 180°.

11. The system of claim 1 wherein said first and said second number are equal.

12. The system of claim 11 wherein said first and second waves also have different frequencies.

13. The system of claim 12 wherein said first symbol has a first frequency and said second signal has a second frequency, said second frequency being an integer multiple of said first frequency.

14. The system of claim 13 wherein said second frequency is double said first frequency.

15. The system of claim 1 further comprising an encoder for encoding binary bits into symbols, each symbol corresponding to more than one binary bit.

16. The system of claim 15 wherein one of said first and second integer numbers is an odd number.

17. The system of claim 1 wherein said first and second waves have equal periods, and wherein said first wave consists of one half cycle and said second wave consists of two half cycles.

18. A data communication system for an implantable device with a housing, said system comprising:

a transmitter disposed in said housing and including a generator for generating a first symbol consisting of a first integer number of half cycles of a first sinusoidal wave having a first frequency and a second symbol consisting of a second integer number of half cycles of a second sinusoidal waves having a second frequency, said second frequency being a multiple of said first frequency.

19. A transmitter for transmitting data from an implanted device, said transmitter comprising:

tank means for defining selectively a first tank circuit having a first resonating frequency, and a second tank circuit having a second resonating frequency;

switching means for selectively activating said first and said second tank circuit in accordance with transmission data to define a first set of symbols having a first frequency and a second set of symbols having a second frequency, each symbol consisting an integer number of half cycles, the symbols of each set including a positive cosine wave and a negative cosine wave; and means for transmitting said symbols.

20. The transmitter of claim 19 wherein said symbols have a preselected duration.

21. The transmitter of claim 19 wherein each said tank circuit includes a capacitor and an inductor, and means for refreshing the energy in said tank circuit at preselected intervals.

22. A data communication system for an implantable device with a housing, said system comprising:

a transmitter disposed in said housing and including a generator for generating a first symbol consisting of a first integer number of a first sinusoidal wave and a second symbol consisting of a second integer number of a second sinusoidal wave, said first and second waves having one of a different phase and frequency; and a receiver having a circuit for distinguishing said first symbol from said second symbol, said circuit including a filter for generating first and second sinusoidal received signals based on said symbols and a comparator for comparing magnitudes of said received signals.

23. A data communication system for an implantable device with a housing, said system comprising:

a transmitter disposed in said housing and including (A) a generator for generating a first symbol consisting of a first integer number of a first sinusoidal wave and a second symbol consisting of a second integer number of a second sinusoidal wave, said first and second waves having one of a different phase and frequency; and (B) a transmitting circuit for transmitting said symbols consecutively, said symbols being arranged in consecutive frames, each frame being preceded by a quiet period.

24. The system of claim 23 further comprising a receiver remote from said transmitter for receiving said symbols, said receiver including a transmitting section transmitting data to said implantable device during said quiet period.

25. A data communication system for an implantable device with a housing, said system comprising:

a transmitter disposed in said housing and including a generator for generating a first symbol consisting of a first integer number of a first sinusoidal wave and a second symbol consisting of a second integer number of a second sinusoidal wave, said first and second waves having one of a different phase and frequency, said symbols defining a signal constellation based on said phase and frequency; and a receiver having a circuit for distinguishing said first symbol from said second symbol based on the position of said symbols on said signal constellation.

26. A communication transceiver for exchanging data between an implantable cardiac device and an external device, said transceiver comprising:

a transmitter transmitting multivalued symbols at a carrier frequency, each symbol having a predetermined symbol period, each symbol corresponding to more than one binary bit, said symbols including a first symbol defined by a first phase and a first frequency and a second symbol defined by a second phase and a second frequency, at least one of said first and second frequencies being higher than said carrier frequency.

27. The communication transceiver of claim 26 further comprising a receiver having a decoder for decoding said symbols into binary data based on a position of said symbols on a point constellation defined by the frequencies and phases of said symbols.

28. The transceiver of claim 26 wherein said symbols are generated cosine waves.

29. A method of transmitting a stream of binary bits from an implantable cardiac device to an external programmer comprising the steps of:

partitioning said binary bits into groups of at least two bits each;

encoding said groups into symbols;

transmitting sinusoidal waves corresponding to said symbols, each symbol being defined by a sinusoidal wave of predetermined phase and frequency;

receiving said sinusoidal waves; and decoding said sinusoidal waves into binary data.

30. The method of claim 29 wherein said sinusoidal waves are transmitted at a carrier frequency, and wherein at least one of said waves has a wave frequency higher than said carrier frequency.

* * * * *